United States Patent
Veronesi et al.

(10) Patent No.: US 10,001,452 B2
(45) Date of Patent: Jun. 19, 2018

(54) AIRCRAFT RESCUE HOIST ROPE DESIGNED FOR CONTINUOUS INSPECTION

(71) Applicant: Goodrich Corporation, Charlotte, NC (US)

(72) Inventors: William A. Veronesi, Hartford, CT (US); Mauro J. Atalla, Wake Forest, NC (US)

(73) Assignee: Goodrich Corporation, Charlotte, NC (US)

( * ) Notice: Subject to any disclaimer, the term of this patent is extended or adjusted under 35 U.S.C. 154(b) by 7 days.

(21) Appl. No.: 14/940,805

(22) Filed: Nov. 13, 2015

(65) Prior Publication Data

US 2017/0138880 A1   May 18, 2017

(51) Int. Cl.
  *G01N 27/20* (2006.01)
  *B64D 1/22* (2006.01)
  (Continued)

(52) U.S. Cl.
  CPC .............. *G01N 27/20* (2013.01); *B64D 1/22* (2013.01); *D07B 1/145* (2013.01); *G01N 27/041* (2013.01); *D07B 2201/2012* (2013.01); *D07B 2201/2044* (2013.01); *D07B 2201/2046* (2013.01); *D07B 2201/2061* (2013.01); *D07B 2201/2062* (2013.01); *D07B 2201/2065* (2013.01); *D07B 2201/2074* (2013.01)

(58) Field of Classification Search
  CPC ... G01N 2203/028; G01N 27/82; D07B 1/145
  See application file for complete search history.

(56) References Cited

U.S. PATENT DOCUMENTS 3,958,455 A     5/1976   Russell
4,684,293 A *   8/1987   Takafuji .................. D07B 1/145
                                                          324/700

(Continued)

FOREIGN PATENT DOCUMENTS

EP    1359248 A2    11/2003
GB    2152088 A      7/1985
(Continued)

OTHER PUBLICATIONS

Extended European Search Report for EP Application No. 16196352.5, dated Apr. 11, 2017, 11 pages.

*Primary Examiner* — Noam Reisner
(74) *Attorney, Agent, or Firm* — Kinney & Lange, P. A.

(57) ABSTRACT

A method of making a hoist cable capable of continuous resistance monitoring includes applying an electrically-insulating material to at least one strand of a wire rope such that a length of the strand is electrically insulated and an end of the strand is electrically conductive. The end of the at least one strand is joined to other strands of the wire rope such that at least two strands are electrically connected at a free end of the wire rope. A method of inspecting the hoist cable includes transmitting a first electrical signal through a first strand from a hoist drum to a free end of the wire rope and receiving the first electrical signal through a second strand at the hoist drum, the first and second strands being electrically connected at the free end. Using the first electrical signal, the resistance of the wire rope is calculated.

17 Claims, 6 Drawing Sheets

(51) Int. Cl.
*G01N 27/04* (2006.01)
*D07B 1/14* (2006.01)

(56) References Cited

U.S. PATENT DOCUMENTS

| | | | |
|---|---|---|---|
| 5,834,942 A * | 11/1998 | De Angelis | D07B 1/025 |
| | | | 187/226 |
| 7,123,030 B2 | 10/2006 | Robar et al. | |
| 7,409,870 B2 | 8/2008 | Stucky et al. | |
| 7,410,033 B2 | 8/2008 | Veronesi et al. | |
| 7,506,728 B2 | 3/2009 | Hawkes et al. | |
| 7,540,359 B2 | 6/2009 | Veronesi et al. | |
| 7,653,506 B2 | 1/2010 | Stucky et al. | |
| 7,801,690 B2 | 9/2010 | Veronesi et al. | |
| 8,011,479 B2 | 9/2011 | Stucky et al. | |
| 8,424,653 B2 | 4/2013 | Stucky et al. | |
| 9,016,665 B2 | 4/2015 | Lin et al. | |
| 2003/0089551 A1* | 5/2003 | Kato | B66B 7/06 |
| | | | 182/1 |
| 2005/0231207 A1* | 10/2005 | Goldwater | D07B 1/145 |
| | | | 324/522 |
| 2011/0089130 A1 | 4/2011 | Stephan | |
| 2014/0027401 A1* | 1/2014 | Ilaka | B66C 13/16 |
| | | | 212/276 |

FOREIGN PATENT DOCUMENTS

| | | |
|---|---|---|
| JP | 2003206085 A | 7/2003 |
| WO | WO 2013119203 A1 | 8/2013 |

* cited by examiner

AIRCRAFT RESCUE HOIST ROPE DESIGNED FOR CONTINUOUS INSPECTION

BACKGROUND

The present invention relates generally to the inspection of load-bearing wire ropes and, more particularly, to continuous inspection of a wire rope having a free end such as a hoist rope used in rescue aircraft.

Continuous resistance monitoring of cables often involves transmitting one or more electrical signals through cables to calculate a resistance. As the cables wear, corrode, or are otherwise mechanically damaged, the resistance of the cables change. When the resistance exceeds a safe range, the cables are removed from service. Continuous resistance monitoring is particularly suited for load-bearing elevator cables. Elevator cables contain a series of parallel-extending and electrically-isolated cables, which permit the electrical signals to traverse the length of the cable. Each end of the elevator cable is anchored to a fixed structure, enabling the ends to be connected electrically to facilitate continuous resistance monitoring of the cable. However, conventional wire ropes are not similarly constructed.

Wire ropes of various sizes and configurations are constructed from a number of strands, each strand helically arranged about a metallic or non-metallic core. Each strand of the wire rope includes a number of wires, which like the strands, are arranged helically about a metallic or non-metallic center. Wire ropes are often wound around a hoist drum at a fixed end and affixed to a lifting hook or other mechanical attachment at the opposing free end. Because wires and strands are helically wound, the wires and strands contact each other along the length of the wire rope. The contact points are electrically-conductive, which short-circuit electrical signals sent from the fixed end of the wire rope and prevent the implementation of continuous inspection methods.

Some wire rope applications, for example conventional hoist ropes used in rescue aircraft, are used to lift loads that, should the wire rope fail, would result in extensive damage, serious injury, or loss of life. Since continuous resistance monitoring cannot be used, conventional wire ropes used in such critical applications are replaced after a predetermined time in service or in accordance with a recorded load history, which are not direct measurements of the mechanical condition of the wire rope. As a result, conventional wire ropes are often replaced prematurely. Therefore, a need exists for a wire rope capable of continuous resistance monitoring such that the wire rope can be replaced based on an actual mechanical condition of the rope.

SUMMARY

A method of making a hoist cable capable of continuous resistance monitoring includes applying an electrically-insulating material to each strand of a wire rope such that a length of each strand is electrically insulated, and at least a first end of each strand is electrically conductive. The method further includes joining the first ends of at least two strands to a lifting hook such that the at least two strands are electrically connected at the lifting hook.

A method of using a wire rope comprising a core strand and a plurality of outer strands encircling the core strand includes transmitting an electrical signal through a first strand from a hoist drum to a free end of the wire rope and receiving the electrical signal through a second strand at the hoist drum. Based on the electrical signal received at the hoist drum, a further step of the method includes calculating the resistance of the wire rope. To facilitate the transmission of the electrical signal, the first and second strands are electrically connected at the free end, and each strand of the wire rope has a discrete layer of electrically-insulating material along at least a portion thereof.

A wire rope capable of being monitored using continuous resistance monitoring includes a core strand, a plurality of outer strands encircling the core strand, and a lifting hook at a free end of the wire rope that mechanically joins the core strand and the plurality of outer strands. Each of the plurality of outer strands has a discrete layer of electrically-insulating material along at least a length of each strand, and at least two of the strands are electrically connected at the free end.

DETAILED DESCRIPTION

Figure 1:
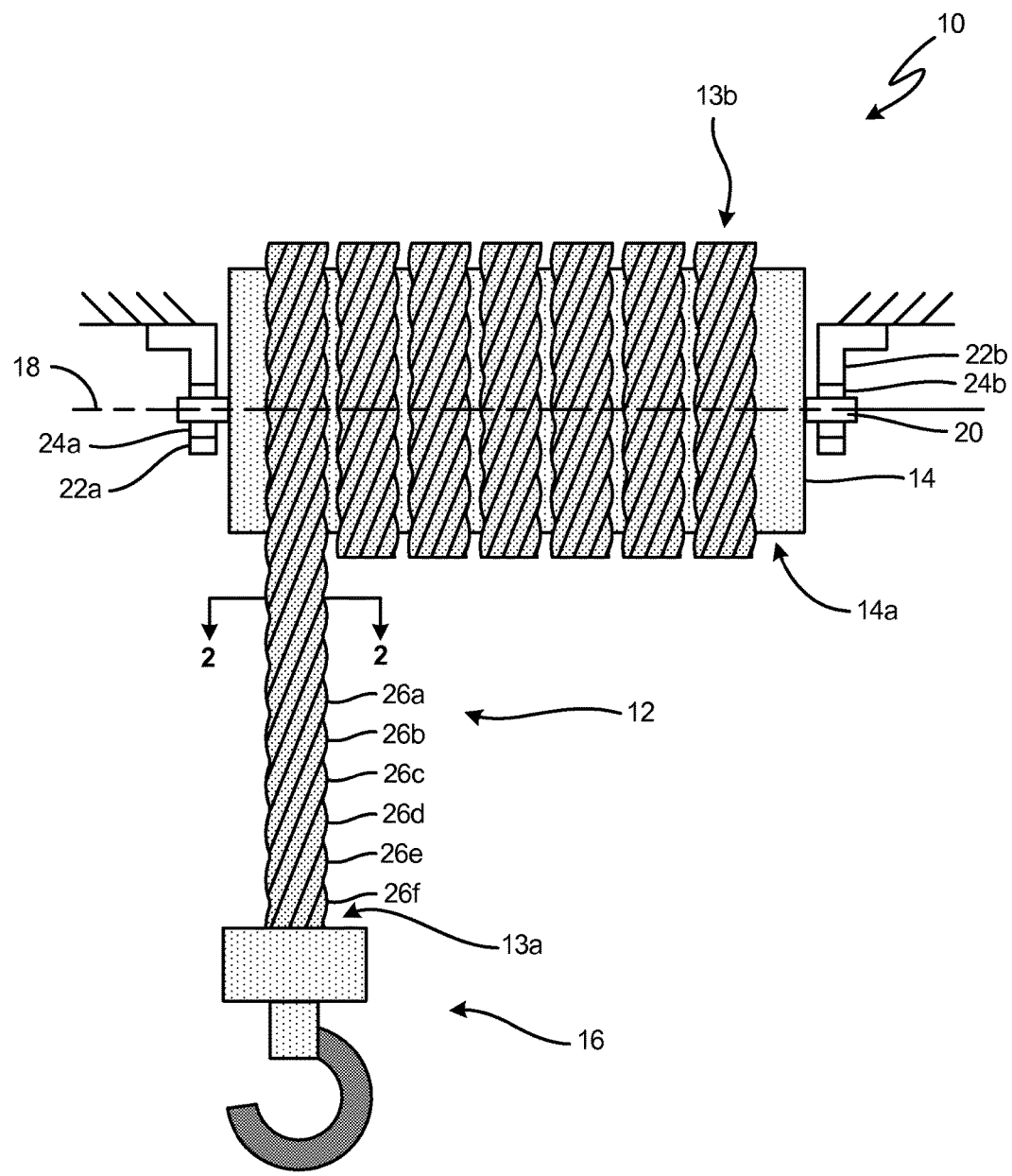
FIG. 1 is a schematic view of a hoist system utilizing a wire rope capable of continuous resistance monitoring.

FIG. 1 is a schematic view of hoist system 10, which includes wire rope 12, drum 14, and lifting hook 16. Wire rope 12 is mechanically coupled to lifting hook 16 at free end 13a and anchored to drum 14 at fixed end 13b. Drum 14 is generally cylindrical and configured to rotate about axis 18. Drum 14 can be supported by any suitable means that facilitates rotation of drum 14 about axis 18. For example, drum 14 can be affixed to shaft 20 and supported at opposing axial ends by supports 22a and 22b in which shaft 20 engages supports 22a and 22b at bearings 24a and 24b, respectively. Supports 22a and 22b are attached to a supporting structure (not shown in FIG. 1), and in some embodiments, supports 22a and 22b are attached to a vehicle such as a helicopter. Drum 14 has outer surface 14a, which is configured to deploy and retract wire rope 12 when drum 14 is driven by a motor or other suitable means. Thus, when drum 16 rotates about axis 18 in a first direction, wire rope 12 deploys whereas when drum 16 rotates about axis 18 in a second direction that is opposite the first direction, wire rope 12 retracts. As such, when a load engages lifting hook 16, wire rope 12 can be used to lift the load.

Wire rope 12 includes one or more strands, each strand containing a plurality of wires. Wire rope 12 can have any conventional wire rope construction that is suitable for the operational service of wire rope 12. For example and as depicted in FIG. 1, standard hoist rope construction includes six outer strands 26a, 26b, 26c, 26d, 26e, and 26f helically wound about core strand 28 (not shown in FIG. 1). Outer strands 26a-f and core strand 28 contain nineteen, helically wound wires (not shown in FIG. 1). As will be described in greater detail below, at least one of outer strands 26a-f and core strand 28 are encased with an electrically-insulating material 30. Optionally, one or more outer strands 26a-f and/or core strand 28 can be enclosed with one or more sleeves (e.g., sleeve 32 and/or sleeves 36a-f as described below), which provides additional electrical insulation, wear resistance, and/or corrosion resistance around electrically-insulating material 30.

Outer strands 26a-f and core strand 28 are mechanically affixed to lifting hook 16 at free end 13a by first stripping material 30 and/or one or more sleeves from free end 13a. Then, outer strands 26a-f and core strand 28 can be attached to hook 16 by swaging strands 26a-f and core strand 28 to hook 16 or by other known means. Attaching all strands to hook 16 in this manner results in outer strands 26a-f and core strand 28 being electrically connected at free end 13b of wire rope 12. Alternatively, pairs can be mechanically joined among outer strands 26a-f and core strand 28 to form one or more electrical circuits within wire rope 12. Each electrically-connected pair of strands is electrically insulated prior to affixing hook 16.

At fixed end 13b, material 30 and/or one or more sleeves are stripped from strands 26a-f and core strand 28 before affixing to drum 14. The connections of each outer strand 26a-f and core strand 28 are electrically-insulating from each other at drum 14 to facilitate sending and receiving electrical signals through wire rope 12.

Figure 2A:
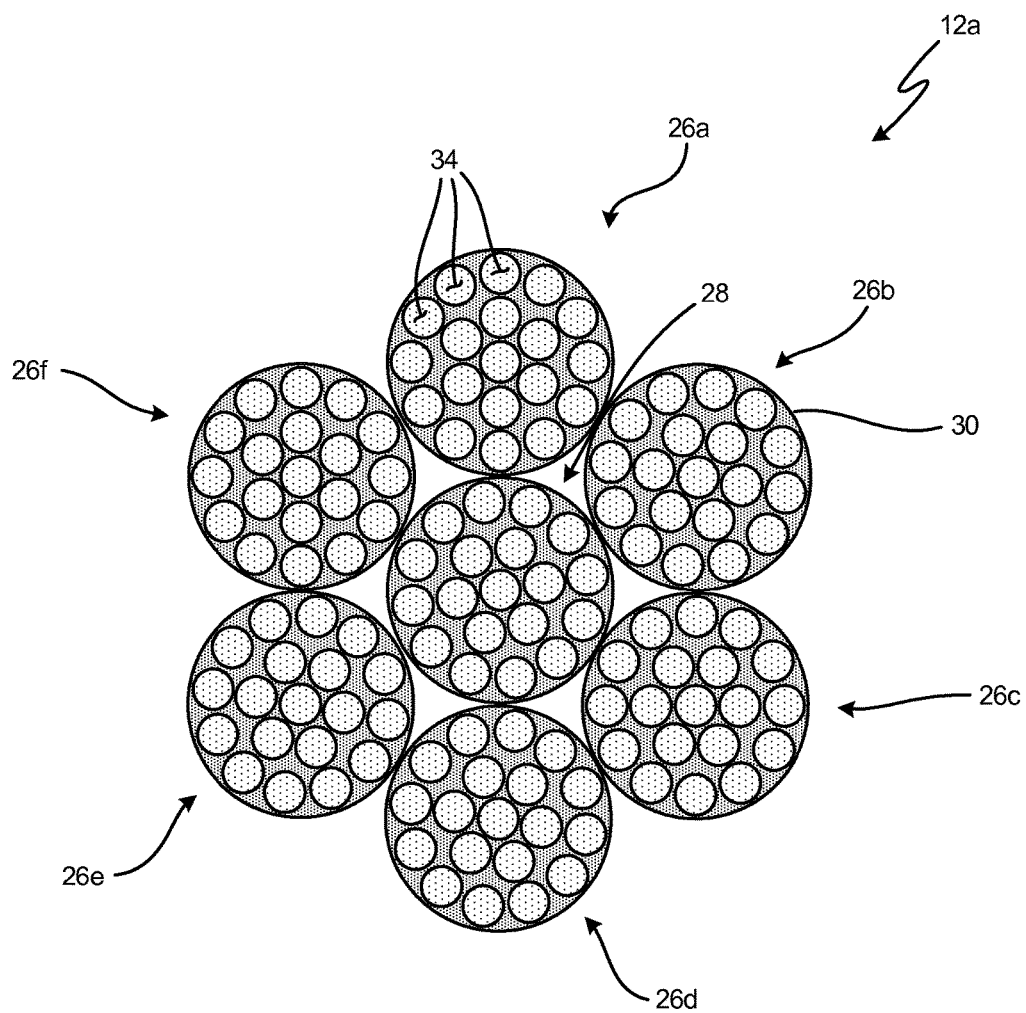
FIG. 2A is a cross-sectional view taken along line 2-2 showing a wire rope having electrically-insulated strands.

FIG. 2A is a cross-sectional view of wire rope 12a taken along line 2-2 in FIG. 1. Wire rope 12a includes outer strands 26a, 26b, 26c, 26d, 26e, and 26f which encircle core strand 28. Outer strands 26a-26f and core strand 28 are encased by material 30, which completely encloses wires 34 contained within core strand 28 and each strand 26a-f. Because each outer strand 26a-f encircles core strand 28, each of strands 26a-f contacts core strand 28. Moreover, each of outer strands 26a-f contacts two adjacent outer strands along the outer periphery of wire rope 12a. For example, outer strand 26a contacts outer strand 26b and 26f on opposing sides of strand 26a, and outer strand 26a contacts core strand 28. Material 30 is electrically-insulating such that outer strands 26a-f and core strand 28 are electrically-insulated from each other along a length of the wire rope between free end 13a and fixed end 13b. With material 30, electrical signals can traverse the length of wire rope 12a along one of the outer strands 26a-f and/or core strand 28 without shorting to an adjacent strand.

The dielectric strength and wear characteristics of material 30 are adapted to the electrical signal strength and service of wire rope 12. As such, the electrical and mechanical properties of material 30 are selected for each application of wire rope 12. In some embodiments, material 30 is thermoplastic polyurethane, which has performed well in hoist rope applications.

Although wire rope 12a encases each strand with material 30, electrically-insulating each outer strand 26a-f and core strand 28 with material 30 is not necessary to transmit electrical signals through wire rope 12a. At a minimum, encasing one wire 34 with material 30 electrically isolates one of wires 34 from the remaining wires 34, outer strands 26a-f, and core strand 28. In this way, an electrical signal can be transmitted through the electrically-insulated wire 34 and received through the remaining wires and strands or vice versa. Encasing a single strand with material 30, whether the strand is one of outer strands 26a-f or core strand 28, improves electrical isolation of wires 34 within that strand, thereby facilitating signal transmission through the insulated strand and receipt of the return signal through the remaining strands or vice versa.

Figure 2B:
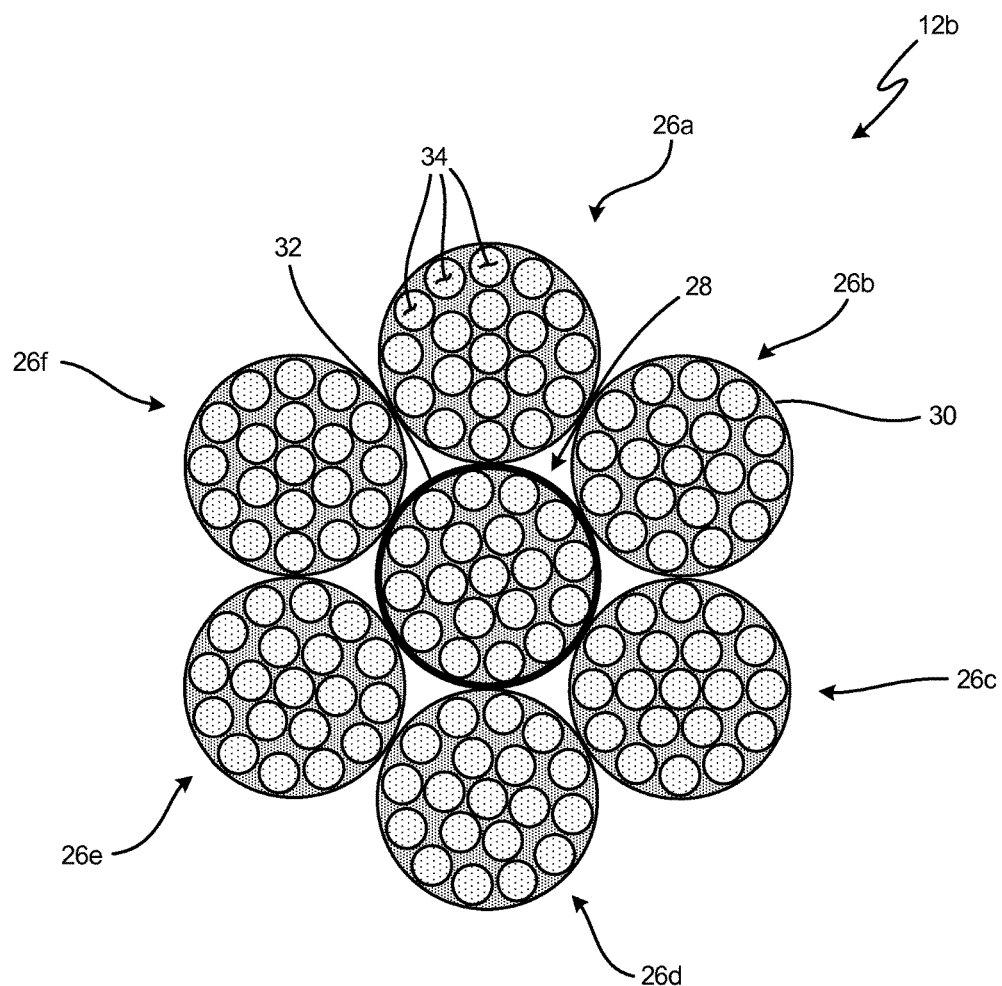
FIG. 2B is a cross-sectional view taken along line 2-2 showing a wire rope having electrically-insulated strands and a wear resistant, corrosion resistant, and/or electrically-insulating sleeve enclosing a core strand.

FIG. 2B is a cross-sectional view of wire rope 12b taken along line 2-2 in FIG. 1. Wire rope 12b also includes outer strands 26a, 26b, 26c, 26d, 26e, and 26f and core strand 28 encased by material 30 as described with reference to wire rope 12a. Wire rope 12b is constructed similarly to wire rope 12a and, additionally, includes sleeve 32 configured about core strand 28. Sleeve 32 increases the wear and corrosion resistance of core strand 28, which is encased with material 30. Sleeve 32 can also be electrically-insulating to increase the dielectric strength of core strand 28 relative to outer strands 26a-f. Core strand 28 is often the subjected to the heaviest wear because it is contacted by each of the outer strands 26a-f. Adding sleeve 32 increases the wear and corrosion resistance of core strand 28, thereby increasing the service life of wire rope 12b. Additionally, increasing the dielectric strength of core strand 28 relative to outer strands 26a-f is particularly useful for continuous resistance monitoring methods which transmit signals from fixed end 13b to free end 13a through core strand 28 and receive signals from free end 13a through one or more outer strands 26a-f.

Alternatively, wire rope 12b could be constructed without material 30, relying only on sleeve 32 to electrically insolate one of outer strands 26a-f and core strand 28 from the remaining strands. Like the alternative embodiment of wire rope 12a which relies on a single strand or wire encased with material 30, a single strand of wire rope 12b surrounded by sleeve 32 facilitates transmission of an electrical signal through the insulated strand and received through one or more of the remaining strands or vice versa.

Figure 2C:
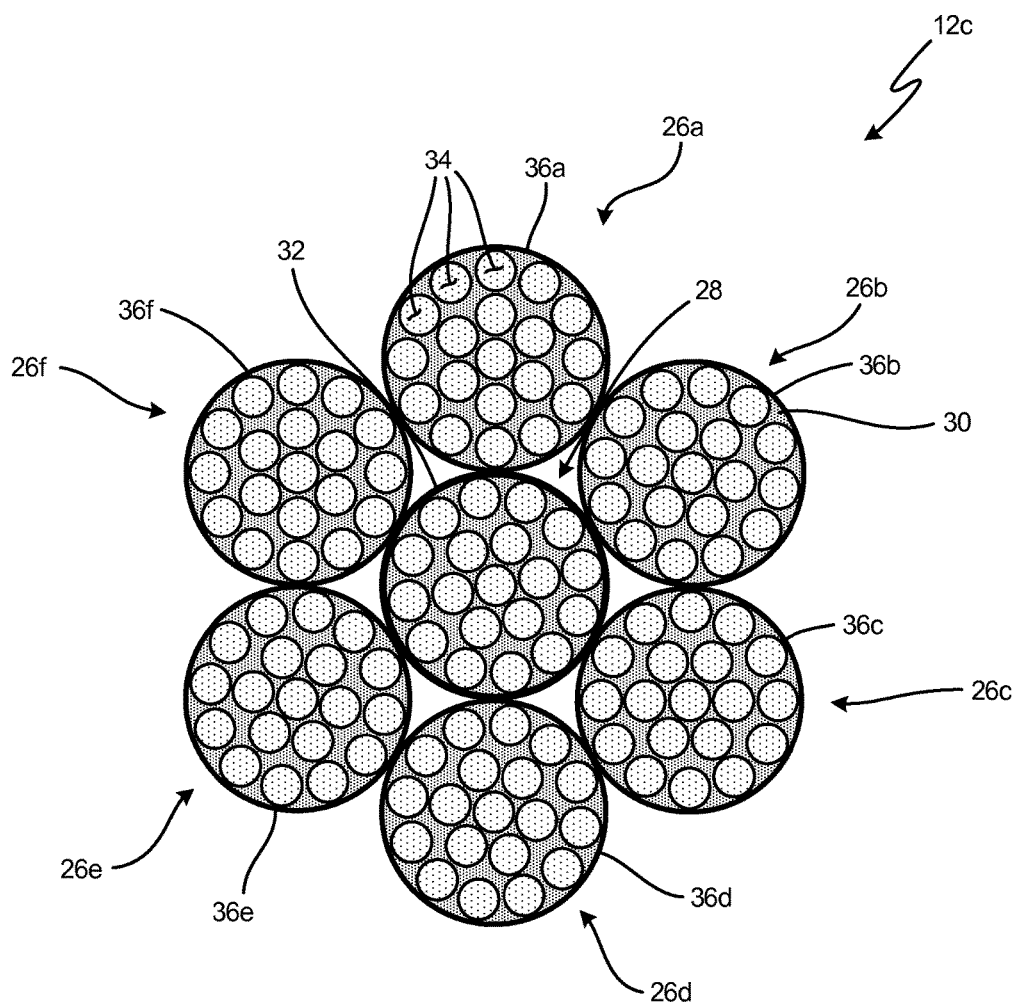
FIG. 2C is a cross-sectional view taken along line 2-2 showing a wire rope having electrically-insulated strands and a wear resistant, corrosion resistant, and/or electrically-insulating sleeve enclosing each strand.

FIG. 2C is a cross-sectional view of wire rope 12c taken along line 2-2 in FIG. 1. Like wire ropes 12a and 12b, wire rope 12c includes outer strands 26a-f and core strand 28 encased by material 30. Wire rope 12c includes sleeve 32 disposed about core strand 28 and outer sleeves 36a, 36b, 36c, 36d, 36e, and 36f, each being disposed about outer strands 26a, 26b, 26c, 26d, 26e, and 26f, respectively. Like sleeve 32, sleeves 36a-f increase the wear resistance of outer strands 26a-f, and can also be electrically-insulating to increase the dielectric strength of each outer strand 26a-f. When sleeves 36a-f are combined with sleeve 32, wire rope 12c provides greater wear and corrosion resistance as compared to the other wire ropes described herein, making wire rope 12c least susceptible to failures from wear and corrosion. Additionally, because the dielectric strength between two adjacent outer strands 26a-f and/or the dielectric strength between one of outer strands 26a-f and core strand 28 are increased, wire rope 12c is particularly suited for continuous resistance methods in which multiple electric signals are transmitted through wire rope 12c.

Figure 3A:
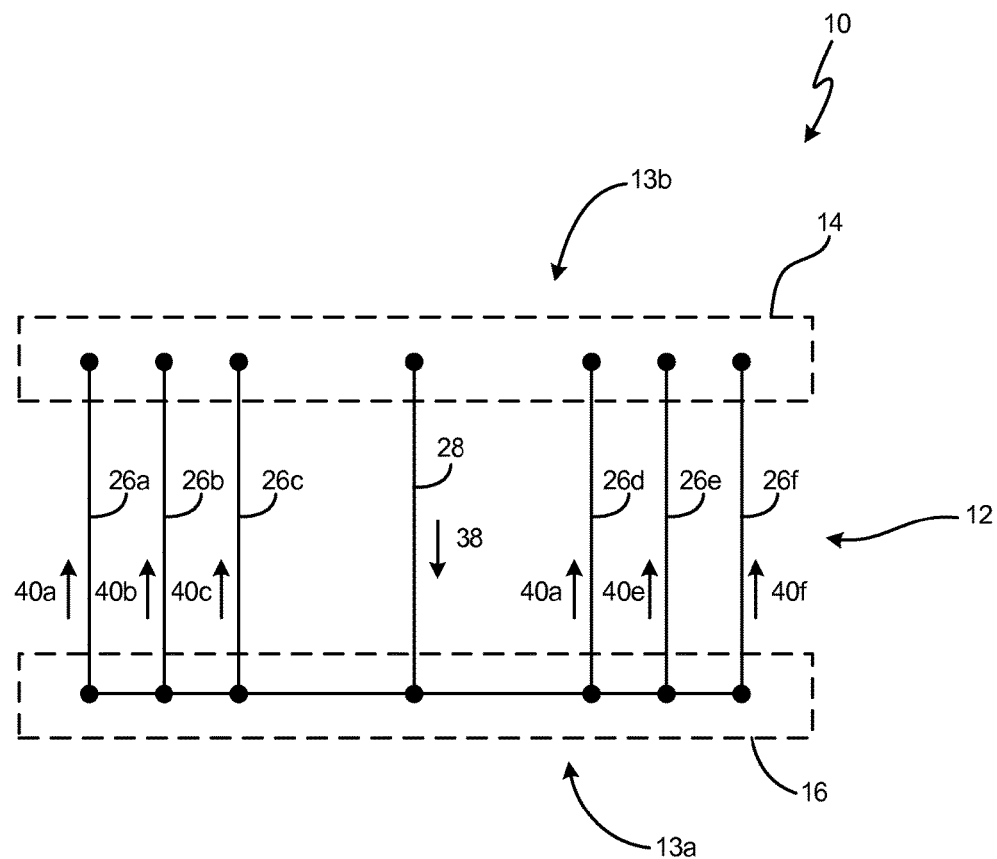
FIG. 3A is a schematic view of a wire rope showing each strand of a wire rope electrically connected at a free end.

FIG. 3A is a schematic showing wire rope 12 in which strands 28a-f and core strand 28 are electrically connected at free end 13a and electrically insulated at fixed end 13b. Wire rope 12 is representative of any of the wire ropes described above. With this configuration, electrical signal 38 is transmitted through core strand 28 to free end 13a, and electrical signals 40a, 40b, 40c, 40d, 40e, and 40f are received at fixed end 13b via outer strands 28a, 28b, 28c, 28d, 28e, and 28f, respectively. In some embodiments, electrical signal 38 is a predetermined electrical current and electrical signals 40a-f are voltages determined between one or more outer strands 28a-f and core strand 28. In other embodiments, electrical signal 38 is a predetermined voltage applied between core strand 28 and one or more outer strands 28a-f, and electrical signals 40a-f are currents measured within core strands 28a-f, respectively. Alternatively, the resistance of wire rope 12 can be determined by transmitting one or more electrical signals 40a-f through outer strands 28a-f, respectively, and receiving signal 38 through core strand 28. In any of the previously-described embodiments, electrical signals 38 and 40a-f are used to calculate the resistance of wire-rope 12, which is proportional to the voltage applied to wire rope 12 and inversely proportional to the current within wire rope 12.

Figure 3B:
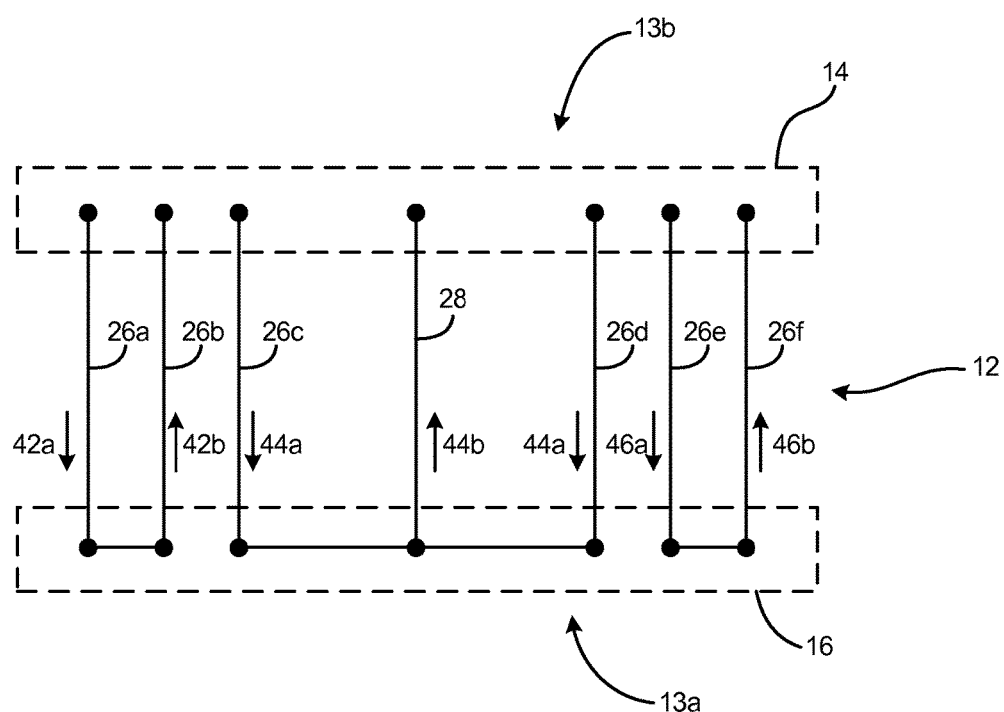
FIG. 3B is a schematic view of a wire rope showing groups of strands electrically connected at a free end and electrically insulated from adjacent strand groups.

FIG. 3B is a schematic view showing wire rope 12 in which groups of strands 26a-f and core strand 28 are electrically connected at free end 13a and electrically insulated from adjacent groups. Like the schematic described with reference to FIG. 3A, wire rope 12 described by FIG. 3B is representative of any of the previously described wire ropes. In some embodiments, outer strands 26a-f are electrically connected to a circumferentially adjacent outer strand. For example, outer strand 26a can be electrically connected to adjacent outer strand 26b. Moreover, outer strands 26c and 26e can be electrically connected to outer strands 26d and 26f, respectively. Additionally, core strand 28 can be included with one of the pairs of outer strands. In the embodiment shown in FIG. 3B, core strand 28 is electrically connected to outer strands 26c and 26d. With this configuration, electrical signals 42a, 44a, and 46a are transmitted through one of the strands within the strand group, and electrical signals 42b, 44b, and 46b are received through another strand within the group. For example, electrical signal 42a can be transmitted through strand 26a, and signal 42b can be received through strand 26b. Similarly, electrical signal 46a can be transmitted through strand 26e, and electrical signal 46b can be received through strand 26f. The strand group containing core strand 28 can send signal 44a through outer strands 26c and 26d, and receive signal 44b through core strand 28. Other combinations of strands are possible. For instance, electrical signals can be transmitted and received through strands on opposing sides of core strand 28, for example, strands 26a and 26d. With any of these configurations, multiple resistances of wire rope 12 can be calculated making it possible to identify which strands within wire rope 12 are damaged, worn, or corroded.

Constructing and using one of wire ropes 12, 12a, 12b, and 12c permits continuous resistance monitoring of the wire rope. With modern manufacturing techniques, the resistance of a wire rope per foot is readily known at the time of manufacture. For additional assurance, the resistance of the wire rope can be determined prior to installation (i.e., at the time of manufacture or installation). Once the wire rope is installed, continuous resistance monitoring includes continuously transmitting and receiving electrical signals through one or more strands of the wire rope at repeated intervals. As the wire rope wears, corrodes, or is damaged, the resistance within the wire rope changes. For instance, worn and damaged strands tend to increase the resistance within the wire rope because the net cross section of some or all of the strands is reduced. Conversely, corrosion tends to increase the electrical conductivity within the wire rope and results in a decreased resistance within the wire rope. Thus, safe operation of the wire rope can be established by a range of resistance values between a minimum resistance and a maximum resistance. When continuous monitoring of the wire rope detects a resistance outside the safe operating range, the wire rope can be removed from service. Thus, replacement of the wire rope is determined based on the actual mechanical condition of the wire rope instead of a preselected time in service or recorded load history. As such, no previous history of the wire rope is needed, allowing operators of the wire rope to evaluate its condition at any time and to avoid premature replacement of the wire rope.

Another advantage of continuous resistance monitoring of wire ropes permits detection of a load attached to the free end. As a wire rope is loaded, the wires within each strand of the wire rope stretch. The stretching reduces the cross-section of each wire and, therefore, increases the resistance through the wire rope. Additionally, as the wire rope is deployed from a drum, a larger length of the wire rope is loaded, the retracted portion of the wire rope transferring a portion of the load to the drum via friction. Thus, the change in resistance between a loaded wire rope and an unloaded wire rope along with the length of wire rope deployed from the drum can be used to determine the load attached at the free end of the wire rope. Using this information, the hoist system can be used to alert operators to overload conditions such as when the wire rope becomes snagged on obstacles during operation or when two much weight is attached to the free end of the wire rope.

With each method of monitoring wire ropes, the resistance of the wire rope varies with the temperature. To increase the accuracy of continuous resistance monitoring and to facilitate evaluation of wire ropes having an unknown wear condition, the temperature of the wire rope could be monitored along with its resistance. For instance, the average temperature of the wire rope could be estimated by installing a temperature sensing device at fixed end 13b of wire rope 12 (see FIG. 1) to measure temperature of one or more of outer strands 26a-f and core strand 28 (not shown in FIG. 1). Other arrangements, such as embedding temperature sensing devices within wire rope 12, using infrared temperature sensing devices, or other known methods, could also facilitate temperature measurement of wire rope 12. In each case, the temperature of wire rope can be used to correct the measured resistance of the rope for temperature.

Discussion of Possible Embodiments

The following are non-exclusive descriptions of possible embodiments of the present invention.

A method of making a hoist cable capable of continuous resistance monitoring includes applying an electrically-insulating material to at least one strand of a wire rope such that a length of the at least one strand is electrically insulated and a first end of the at least one strand is electrically conductive. The method further includes joining the first end of at least two strands at a free end such that the at least two strands are electrically connected at the free end.

The method of the preceding paragraph can optionally include, additionally and/or alternatively, any one or more of the following features, configurations and/or additional components:

A further embodiment of the forgoing method, wherein applying the electrically-insulating material to each strand of the wire rope can result in a second end of each strand that is electrically conductive.

A further embodiment of the foregoing method can further include applying an electrically insulating material to each strand of the wire rope such that a length of each strand is electrically insulated and at least a first end of each strand is electrically conductive. The method can further include joining the first ends of at least two strands to the free end such that the at least two strands are electrically connected at the free end.

A further embodiment of any of the foregoing methods can further include joining second ends of each strand to a hoist drum configured to deploy and to retract the wire rope.

A further embodiment of any of the foregoing methods, wherein the second ends of each strand can be electrically-insulated from each other.

A further embodiment of any of the foregoing methods can further include encasing a core strand with an electrically-insulating sleeve between the first and second ends thereof.

A further embodiment of any of the foregoing methods, wherein the core strand can be centrally located with respect to the other strands.

A further embodiment of any of the foregoing methods can further include encasing each strand with one of a plurality of electrically-insulating sleeves between the first and second ends.

A further embodiment of any of the foregoing methods, wherein the first ends can be joined at the free end such that all of the strands are electrically connected to each other and electrically insulated from the other strands.

A further embodiment of any of the foregoing methods can further include arranging a core strand centrally with respect to a plurality of outer strands.

A further embodiment of any of the foregoing methods, wherein each strand can have a discrete layer of the electrically-insulating material disposed around an outer periphery thereof.

A further embodiment of any of the foregoing methods, wherein the discrete layers of each outer strand can contact the discrete layer of the core strand and the discrete layers of two adjacent outer strands.

A further embodiment of any of the foregoing methods, wherein a lifting hook is attached to the free end of the wire rope.

A method of using a wire rope comprising a core strand and a plurality of outer strands encircling the core strand, each outer strand and core strand having a discrete layer of electrically-insulating material along at least a portion thereof includes transmitting a first electrical signal through a first strand from a hoist drum to a free end of the wire rope. The method further includes receiving the first electrical signal through a second strand at the hoist drum in which the first and second strands are electrically connected at the free end. The method additionally includes calculating a first resistance within the wire rope based on the first electrical signal.

The method of the preceding paragraph can optionally include, additionally and/or alternatively, any one or more of the following features, configurations and/or additional components:

A further embodiment of the foregoing method, wherein the first strand can be the core strand and the second strand can be one of the outer strands.

A further embodiment of any of the foregoing methods, wherein the first electrical signal can be transmitted through each of the outer strands.

A further embodiment of any of the foregoing methods, wherein transmitting the first electrical signal through the first strand can include causing a predetermined current to flow through the first and second strands.

A further embodiment of any of the foregoing methods, wherein receiving the first electrical signal through the second strand can include measuring a voltage across the first and second strands.

A further embodiment of any of the foregoing methods can further include detecting damage within the wire rope if the first resistance exceeds a maximum resistance or if the first resistance is less than a minimum resistance.

A further embodiment of any of the foregoing methods, wherein safe operation of the wire rope can be defined by a set of resistance values between the maximum resistance and the minimum resistance.

A further embodiment of any of the foregoing methods can further include calculating a load applied to the wire rope based on one or more of the first resistance and a drum angle, the drum angle being proportional to a length of wire rope unwound from the hoist drum.

A further embodiment of any of the foregoing methods can further include transmitting a second electrical signal through a third strand from the hoist drum to a free end.

A further embodiment of any of the foregoing methods can further include receiving the second electrical signal through a fourth strand.

A further embodiment of any of the foregoing methods, wherein the third and fourth strands can be electrically connected at the free end.

A further embodiment of any of the foregoing methods, wherein the third and fourth strands can be electrically insulated from the first and second strands.

A further embodiment of any of the foregoing methods can further include calculating a second resistance within the wire rope based on the second electrical signal.

A wire rope capable of being monitored using continuous resistance monitoring includes a core strand, a plurality of outer strands encircling the core strand, and a lifting hook at a free end of the wire rope that mechanically joins the core strand and the plurality of outer strands. The core strand and each of the outer strands have a discrete layer of electrically-insulating material along at least a length of each strand. At least two of the strands are electrically connected at the free end.

The wire rope of the preceding paragraph can optionally include, additionally and/or alternatively, any one or more of the following features, configurations and/or additional components:

A further embodiment of the foregoing wire rope can further include a hoist drum to which each outer strand and core strand is mechanically connected.

A further embodiment of any of the foregoing wire ropes, wherein each strand can be electrically insulated from the other strands at the hoist drum.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A method of making a hoist cable capable of continuous resistance monitoring, the method comprising:
   arranging a core strand centrally with respect to a plurality of outer strands to form a wire rope, wherein each of the plurality of outer strands are helically wound about the core strand, and wherein each of the outer strands and core strand comprises a plurality of wires helically wound about a core wire centrally located with respect to the plurality of wires;
   applying a discrete layer of an electrically-insulating material to an outer periphery of each of the plurality of outer strands and the core strand such that a length of each of the outer strands and the core strand is electrically insulated, and a first end of each of the outer strands and the core strand is electrically conductive; and joining each of the wires at the first ends of at least two strands of the plurality of outer strands and the core strand at a free end of the wire rope such that each wire in the at least two strands of the wire rope are electrically connected at the free end.

2. The method of claim 1, wherein:
applying the electrically-insulating material to the outer strands and the core strand of the wire rope results in a second end of each of the outer strands and the core strand that is electrically conductive; and the method further comprising:
joining the second ends of the plurality of outer strands and the core strand to a hoist drum configured to deploy and to retract the wire rope, wherein each of the second ends of the outer strands and the core strand is electrically insulated from other strands of the wire rope.

3. The method of claim 1 and further comprising:
encasing the electrically-insulating material of the core strand with an electrically-insulating sleeve between the first and second ends thereof.

4. The method of claim 3 and further comprising:
encasing each of the plurality of outer strands and the core strand with one of a plurality of electrically-insulating sleeves between the first and second ends.

5. The method of claim 1, wherein the first ends are joined at the free end such that all of the strands are electrically connected to each other.

6. The method of claim 1, wherein the first ends are joined at the free end such that a plurality of strand pairs are electrically connected to each other and electrically insulated from the other strands.

7. The method of claim 1, wherein a lifting hook is attached to the free end of the wire rope.

8. A method of using a wire rope comprising a core strand and a plurality of outer strands encircling the core strand, each strand comprising a plurality of wires helically wound about a core wire centrally located with respect to the plurality of wires, the method comprising:
transmitting a first electrical signal through each unbroken wire of a first strand from a hoist drum to a free end of the wire rope, wherein the first strand is electrically isolated from adjacent strands by a discrete layer of electrically-insulating material encapsulating an outer periphery of the first strand;
receiving the first electrical signal through each unbroken wire of a second strand at the hoist drum, wherein the wires of the first and second strands are electrically connected at the free end; and
calculating a first resistance within the wire rope based on the first electrical signal.

9. The method of claim 8, wherein the first strand is the core strand and the second strand is one of the plurality of outer strands.

10. The method of claim 9, wherein the first electrical signal is transmitted through each of the plurality of outer strands.

11. The method of claim 8, wherein:
transmitting the first electrical signal through a first strand includes causing a predetermined current to flow through the first and second strands; and
receiving the first electrical signal through the second strand includes measuring a voltage across the first and second strands.

12. The method of claim 8, wherein:
transmitting the first electrical signal through a first strand includes applying a predetermined voltage across the first and second strands; and
receiving the first electrical signal through the second strand includes measuring a current flowing through the first and second strands.

13. The method of claim 8 and further comprising:
detecting damage within the wire rope if the first resistance exceeds a maximum resistance or if the first resistance is less than a minimum resistance, wherein safe operation of the wire rope is defined by a set of resistance values between the maximum resistance and the minimum resistance.

14. The method of claim 8 and further comprising:
calculating a load applied to the wire rope based on one or more of the first resistance and a drum angle, the drum angle being proportional to a length of wire rope unwound from the hoist drum.

15. The method of claim 8 and further comprising:
transmitting a second electrical signal through a third strand from the hoist drum to the free end;
receiving the second electrical signal through a fourth strand, wherein the third and fourth strands are electrically connected at the free end, and wherein the third and fourth strands are electrically-insulated from the first and second strands; and
calculating a second resistance within the wire rope based on the second electrical signal.

16. A wire rope capable of being monitored using continuous resistance monitoring, the wire rope comprising:
a core strand;
a plurality of outer strands encircling the core strand, wherein each of the outer strands and the core strand includes a plurality of wires helically wound about a core wire centrally located with respect to the plurality of wires, and wherein an outer periphery of the core strand and each of the plurality of outer strands have a discrete layer of electrically-insulating material along at least a length of each strand; and
a lifting hook at a free end of the wire rope that mechanically joins the core strand and the plurality of outer strands, wherein each wire within at least two of the strands are electrically connected at the free end.

17. The wire rope of claim 16, and further comprising:
a hoist drum to which each strand is mechanically connected, and wherein each strand is electrically insulated from the other strands at the hoist drum.

* * * * *